United States Patent
Seiler et al.

(10) Patent No.: US 9,968,484 B2
(45) Date of Patent: May 15, 2018

(54) DEVICE AND PROCESS FOR MACHINING THE CORNEA OF A HUMAN EYE WITH FOCUSED PULSED LASER RADIATION

(75) Inventors: Theo Seiler, Zurich (CH); Mathias Woelfel, Erlangen (DE); Christof Donitzky, Eckental/Eschenau (DE)

(73) Assignee: Wavelight GmbH (DE)

( * ) Notice: Subject to any disclaimer, the term of this patent is extended or adjusted under 35 U.S.C. 154(b) by 577 days.

(21) Appl. No.: 13/984,392

(22) PCT Filed: Feb. 15, 2011

(86) PCT No.: PCT/EP2011/000710
§ 371 (c)(1),
(2), (4) Date: Aug. 8, 2013

(87) PCT Pub. No.: WO2012/110050
PCT Pub. Date: Aug. 23, 2012

(65) Prior Publication Data
US 2013/0324984 A1    Dec. 5, 2013

(51) Int. Cl.
*A61F 9/008* (2006.01)
*A61F 2/14* (2006.01)

(52) U.S. Cl.
CPC ...... *A61F 9/00836* (2013.01); *A61F 9/00831* (2013.01); *A61F 2/147* (2013.01); *A61F 2009/00872* (2013.01)

(58) Field of Classification Search
None
See application file for complete search history.

(56) References Cited

U.S. PATENT DOCUMENTS 5,722,971 A * 3/1998 Peyman .................. A61F 2/147
  128/898
5,824,086 A * 10/1998 Silvestrini ............. A61F 9/0017
  606/107

(Continued)

FOREIGN PATENT DOCUMENTS

| WO | 2003005920 A1 | 1/2003 |
| WO | 2008072092 A2 | 6/2008 |
| WO | 2012110050 A1 | 8/2012 |

OTHER PUBLICATIONS

International Search Report and Written Opinion; PCT/EP2011/000710; dated Nov. 15, 2011.

(Continued)

*Primary Examiner* — Lynsey Eiseman
*Assistant Examiner* — Qingjun Kong
(74) *Attorney, Agent, or Firm* — Keiko Ichiye (57) ABSTRACT

A device for machining the cornea of a human eye with focused pulsed laser radiation includes controllable components, a control computer for controlling these components and a control program for the control computer. The control program contains instructions that are designed to generate an incision figure in the cornea permitting the insertion of an intrastromal corneal ring implant. The incision figure includes a ring incision situated totally deep within the corneal tissue and an opening incision extending at right angles to the ring plane of the ring incision from the anterior surface of the cornea or from the posterior surface of the cornea as far as at least the ring incision. The ring incision exhibits, assigned to the opening incision, a radial—relative to the ring axis—widening zone in which the opening incision impinges on the ring incision.

24 Claims, 3 Drawing Sheets (56) References Cited

U.S. PATENT DOCUMENTS

| | | | | |
|---|---|---|---|---|
| 5,855,604 | A * | 1/1999 | Lee | A61F 2/147 |
| | | | | 606/166 |
| 6,206,919 | B1 * | 3/2001 | Lee | A61F 2/147 |
| | | | | 623/4.1 |
| 2002/0055753 | A1 * | 5/2002 | Silvestrini | A61F 2/147 |
| | | | | 606/166 |
| 2003/0014042 | A1 * | 1/2003 | Juhasz | A61F 2/147 |
| | | | | 606/5 |
| 2007/0219542 | A1 | 9/2007 | Yahagi et al. | |

OTHER PUBLICATIONS

Ziemer Ophthalmic Systems AG; Modular architecture; Corneal applications; http://www.femtoldv.com/corneal-applications-z6.html; p. 1; (Aug. 2013).

Sanchez and Naranjo; Intralase FS Laser for ICR Implantation; Cover Story; Cataract and Refractive Surgery Today; pp. 48-50 (Jul. 2005).

Technolas Perfect Vision; Technolas Femtosecond Workstation 520F; pp. 2; (Sep. 2009).

* cited by examiner

DEVICE AND PROCESS FOR MACHINING THE CORNEA OF A HUMAN EYE WITH FOCUSED PULSED LASER RADIATION

TECHNICAL FIELD

The invention is concerned with the generation of incisions in the human cornea by means of focused pulsed laser radiation. In particular, the invention is concerned with the preparation of incisions that permit the insertion of an intrastromal corneal ring implant.

BACKGROUND

For the purpose of treating diseases of the human eye, such as, for example, keratotonus, and also for the purpose of eliminating mild forms of defective vision, above all myopia (short-sightedness), it is known to insert annular intrastromal corneal implants into a ring tunnel in the corneal tissue expressly created for them. In the state of the art, diverse configurations of such corneal ring implants are known which may differ, inter alia, by virtue of their peripheral length (closed ring, slotted ring, semi-ring or ring segment of different length), by virtue of their cross-sectional shape (e.g. circular, oval, triangular, hexagonal), by virtue of their cross-sectional progression in the peripheral direction (constant cross-section or variable cross-section, such as, for example, in the case of a sickle), by virtue of their material, and by virtue of whether they have a fixed cross-sectional shape and size or are adjustable in this respect. The implant may be in one piece or may consist of several separate ring segments (e.g. semi-rings) which are implanted in succession in the peripheral direction. A feature all these ring implants have in common is that they extend along a ring arc, customarily—but not necessarily—having a circular-arc-shaped curvature. By way of material, use is often made nowadays of PMMA (polymethyl methacrylate), in which connection other biocompatible materials have already been tried in the past and are, within the scope of the invention, by no means ruled out. The invention is generally applicable for arbitrary intrastromal corneal ring implants; there is no restriction to particular types.

In order that the ring implant can be inserted into the cornea, firstly a suitable ring tunnel (channel) with a peripheral length at least corresponding to the implant to be inserted has to be prepared in the stroma. In accordance with one method this may be accomplished by the operating surgeon manually with a suitable mechanical tool with which the stromal tissue layers can be separated from one another (e.g. spatula).

Laser-assisted cutting systems have recently become available with which it has become possible to place incisions and entire incision figures, in themselves of arbitrary two-dimensional or even three-dimensional configuration, in human ocular tissue and, above all, in the corneal issue and also in the lens tissue. The focused laser radiation employed in this connection is of ultra-short-pulse nature (with pulse durations within the femtosecond range) and has to have a wavelength in respect of which the tissue to be machined is transmissive. Wavelengths that are frequently employed lie within the near-infrared region (e.g. between 1 µm and 1.1 µm), but ultraviolet wavelengths above about 300 nm and also higher infrared wavelengths between approximately 1600 nm and 1700 nm are also possible for the preparation of incisions in the cornea or in the human lens.

For the generation of incisions by means of focused laser radiation in transparent material (transparent to the laser radiation), the so-called laser-induced optical breakthrough is utilised by way of physical effect. This results in a local vaporisation of the irradiated material, which is designated as photodisruption. The photodisruption is spatially restricted substantially to the area of the focus. By placing a plurality of such photodisruptions side by side, the most diverse incision figures can be generated.

The photodisruptive generation of incisions in the human cornea by means of ultra-short-pulse focused laser radiation has, for example, been proposed many times for the preparation of the flap in the course of a LASIK operation (LASIK: laser in-situ keratomileusis).

SUMMARY OF EXAMPLE EMBODIMENTS

It is the object of the invention to demonstrate a way in which the preparatory machining of the cornea that is necessary for the insertion of an intrastromal corneal ring implant can be carried out in a manner that is reliable and that burdens the patient as little as possible.

With a view to achieving this object, the invention provides a device for machining the cornea of a human eye with focused pulsed laser radiation, with controllable components for setting the location of the radiation focus, with a control computer for controlling these components and with a control program for the control computer, the control program containing instructions that are designed to bring about, upon execution by the control computer, the generation of an incision figure in the cornea permitting the insertion of an intrastromal corneal ring implant, the incision figure comprising at least one ring incision situated totally deep within the corneal tissue and also at least one opening incision extending at right angles to the ring plane of the ring incision from the anterior surface of the cornea or from the posterior surface of the cornea as far as at least the ring incision, the ring incision exhibiting, assigned to the opening incision, a radial—relative to the ring axis—widening zone, and the opening incision in the widening zone impinging on the ring incision.

The opening incision may pass through either as far as the anterior surface of the cornea or as far as the posterior surface of the cornea. In the former case the implant can be introduced into the opening incision directly from outside the eye; in the latter case, through the anterior chamber of the eye, for which purpose a separate incision into the eye is required in order to introduce the implant into the anterior chamber.

The invention makes it possible to generate by laser technology all the channels that have to be created in the cornea in order to be able to insert an intrastromal corneal ring implant. The human factor and the sources of error associated therewith, which, for example, are unavoidable in the case of manual generation of the tunnel, can be very largely excluded in this way. This ensures reliably good surgical outcomes. Besides, the less the operating surgeon machines the eye with a mechanical tool, the more agreeable does the operation appear for the patient. In this connection the dispensing with any manually performed incisions constitutes a considerable gain in comfort on the part of the patient.

In accordance with the invention the incision figure generated by laser technology comprises at least one ring incision serving to receive the implant to be inserted, the peripheral length of which accordingly corresponds to at least that of the implant. It will of course be understood that the peripheral length of the ring incision may be greater than the peripheral length of the implant. Preferentially, the central periphery of the ring incision corresponds to that of the implant. The reference to at least one ring incision illustrates the fact that the incision figure may, if desired, exhibit several (at least two) ring incisions, which each serve to receive an implant.

The ring incision lies totally within the cornea. In order to create an access to the ring incision, the incision figure generated by laser technology includes, in addition, an opening incision which extends from the anterior surface of the cornea or from the posterior surface of the cornea (i.e. from the anterior chamber of the eye) as far as at least the ring incision. This opening incision creates an implantation opening into the corneal tissue, through which the implant can be introduced. The opening incision runs at right angles to the ring plane of the ring incision. Provided that the incision figure is generated in an applaned (levelled) state of the cornea, the ring incision can be generated, for example, in a plane that is parallel to the levelled region of the corneal surface. The opening incision may, in turn, for example, run perpendicular to this plane, i.e. the direction of its extent from the corneal surface as far as the ring incision may lie perpendicular to this plane.

The ring incision may be a planar or a non-planar incision. Its incision surface may (at least in the applaned state of the cornea) lie, for example, parallel to a ring plane perpendicular to the ring axis. It will be understood that, depending on the cross-sectional shape of the implant to be inserted, the incision surface of the ring incision may also be oriented, at least along a part of the ring periphery, obliquely relative to such a ring plane. With a view to avoiding post-operative displacements of the inserted implant, under certain circumstances incision geometries of the ring incision are conceivable that bring about a positive or force-closed fixation of the implant in the ring incision. The cross-sectional geometry of the ring incision does not have to be constant over the entire peripheral length thereof (the term 'peripheral length' relates here to the peripheral direction of the ring); it may alternatively be variable in the peripheral direction of the ring. Overall, in a good approximation it may be said that the ring incision in the corneal tissue constitutes an approximately washer-shaped slot for receiving the implant, in which connection the term 'ring incision' here is by no means to be understood in such a way that the ring incision has to extend over a full ring periphery, but rather it may alternatively extend only over a part of a full ring periphery, for example approximately over half of a ring periphery.

In places where the opening incision impinges on the ring incision the ring incision has a radial widening zone (radial relative to the ring axis). The ring incision is accordingly designed to be wider in the widening zone than in other peripheral regions. The presence of the widening zone makes it easier to thread the implant into the ring incision from the opening incision. The radially inside or/and outside edge of the widening zone may, for example, exhibit a circular-arc-shaped contour, a sawtooth-shaped contour or a bulbous/spheroidal contour.

The widening zone preferably forms, radially inside and outside, a radial widening of the ring incision in comparison with regions of the ring incision adjoining in the peripheral direction. It will of course be understood that in alternative configurations the widening zone may form such a radial widening in comparison with the adjoining regions of the ring incision solely radially inside or solely radially outside.

The peripheral length of the widening zone is preferentially small in comparison with the peripheral length of the ring incision, whereby the ring incision may have continuously smaller radial width outside the widening zone than in the widening zone. For example, the peripheral length of the widening zone may amount to at most twenty percent, better at most fifteen percent and still better at most ten percent, of the peripheral length of the ring incision overall. Outside the widening zone the ring incision may have constant radial width in the peripheral direction.

The opening incision is—when viewed in an axial cross-section—preferentially oriented substantially radially relative to the ring axis; alternatively it may, of course, also be oriented obliquely relative to the ring axis (again when viewed in a cross-section perpendicular to the ring axis).

The opening incision may have a planar or a non-planar incision surface, this incision-surface geometry relating to an applaned state of the cornea in which the latter is resting on a planar contact surface of a contact element of the device according to the invention that is transparent to the laser radiation.

It is advisable if the opening incision crosses the ring incision in the direction from the anterior surface or posterior surface of the cornea and extends beyond said ring incision. In this configuration the opening incision consequently extends more deeply into the cornea than the widening zone of the ring incision. In this manner an open passageway from the opening incision to the ring incision can be guaranteed at any time.

In a preferred configuration the opening incision impinges on the ring incision in a region of greatest radial width of the widening zone and extends there substantially over the entire radial width of the widening zone. Generally it is expedient if the width of the opening incision—measured at right angles to the longitudinal extent from the anterior surface or posterior surface of the cornea as far as the ring incision—is greater than the radial width of the ring incision. This simplifies the introduction of the implant. According to one configuration, the width of the opening incision may correspond substantially to the maximal radial width of the widening zone. It will of course be understood that the opening incision may optionally be narrower or wider than the maximal radial width of the widening zone. Equally, the opening incision may impinge on the ring incision totally within the widening zone and may alternatively extend beyond the widening zone radially inside or/and radially outside.

Over its longitudinal extent the opening incision preferentially has constant width. Alternatively, a variable width of the opening incision is nevertheless also conceivable; for example, it may have increasingly greater width towards the anterior surface or posterior surface of the cornea.

The opening incision may, when viewed in the direction from the anterior surface or posterior surface of the cornea to the ring incision, run substantially rectilinearly or it may, in such an view, run at least along a portion in curved manner or/and bending sharply.

The ring incision may form a ring that is closed in the peripheral direction or alternatively may form only a partial ring.

The incision figure may include at least one ring incision, to which a single opening incision is assigned. Alternatively or additionally, the incision figure may include at least one ring incision, to which two or more opening incisions are assigned. For example, the incision figure may exhibit a ring incision with two opening incisions which in diametrically opposed widening zones or/and in the region of opposite peripheral ends of the ring incision impinge on the latter.

The laser radiation that is preferentially used has pulse durations within the range of less than one picosecond, for example within the low three-digit femtosecond range.

BRIEF DESCRIPTION OF THE DRAWINGS

The invention will be elucidated further in the following on the basis of the appended drawings. Represented are.

DETAILED DESCRIPTION OF THE DRAWINGS

Figure 1:
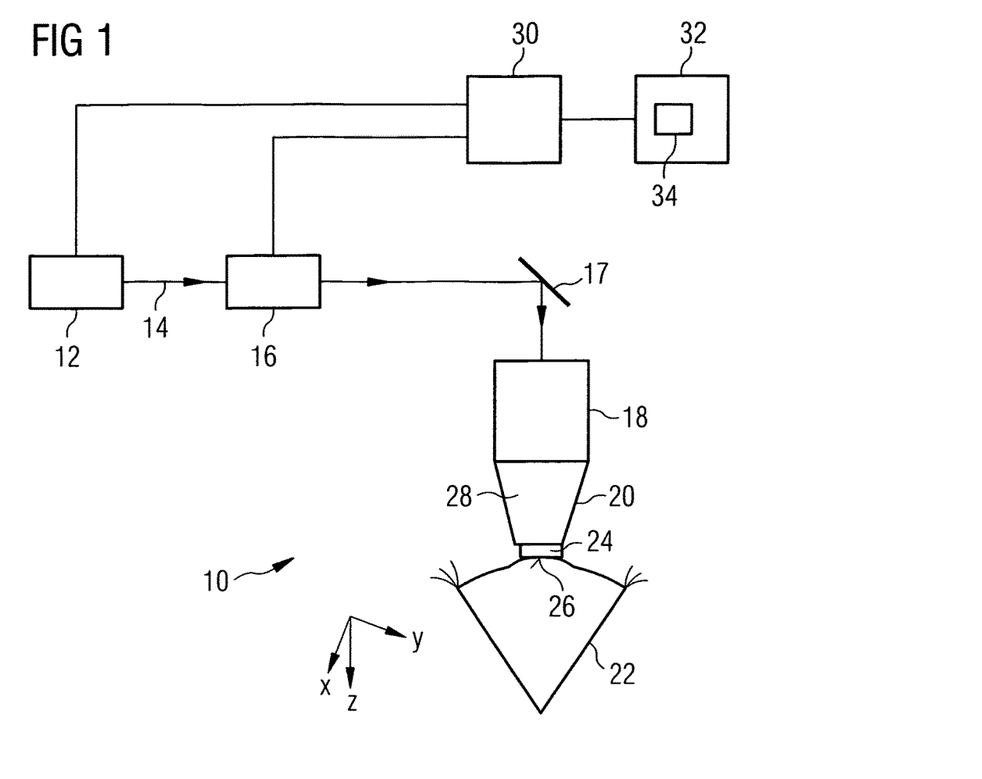
FIG. 1: schematically, an exemplary embodiment of a device for generating incisions in the tissue of a human eye by laser technology.

The laser device shown in FIG. 1 denoted generally by 10 includes a laser source 12 which generates a laser beam 14 with pulse durations within the femtosecond range. In the beam path of the laser beam 14 a series of optical components are arranged, inter alia a scanner 16, indicated here as a unified functional block, an immovable deflecting mirror 17 and also a focusing objective 18. The scanner 16 serves for transverse and longitudinal control of the location of the focal point of the laser beam 14. 'Transverse' designates a direction at right angles to the direction of propagation of the laser beam 14; 'longitudinal', on the other hand, means a progression in the direction of beam propagation. In conventional notation the traverse plane is spanned by mutually perpendicular direction arrows x, y, whereas the longitudinal direction is designated as the z-direction.

For transverse deflection, i.e. x-y deflection, of the laser beam 14 the scanner 16 may, for example, include a pair of galvanically actuated scanner mirrors (not represented in any detail) which are arranged to be tiltable about mutually perpendicular axes. Alternatively, a transverse deflection, for example by means of an electro-optical crystal, is conceivable.

For the z-control of the focus position the scanner 16 may, for example, contain a longitudinally adjustable lens or a lens of variable refractive power or a deformable mirror, with which the divergence of the laser beam 14 and consequently the z-position of the beam focus can be influenced. It will be understood that the components of the scanner 16 serving for the transverse focus control and for the longitudinal focus control may be distributed along the beam path of the laser beam 14 and, in particular, divided up to different structural units. For example, the function of the z-focus adjustment may be fulfilled by an optical component arranged in beam-expanding optics (beam expander, e.g. Galilean telescope), whereas the optical components serving for the transverse focus control may have been accommodated in a separate structural unit between the beam-expanding optics and the focusing objective 18. The representation of the scanner 16 as a unified functional block in FIG. 1 serves merely for better clarity of layout.

The focusing objective 18 is preferably an f-theta objective and is preferentially detachably coupled on its beam-exit side with a patient adapter 20. The patient adapter 20 constitutes an abutment interface for the cornea of an eye 22 to be treated. For this purpose said patient adapter exhibits a contact element 24 that is transparent to the laser radiation and that on its underside facing towards the eye constitutes an abutment surface 26 for the cornea. In the exemplary case that is shown, the abutment surface 26 is realised as a plane surface and serves for levelling the cornea, by the contact element 24 being pressed against the eye 22 with appropriate pressure or by the cornea being aspirated onto the abutment surface 26 by underpressure.

The contact element 24 (in the case of plane-parallel design, customarily designated as the applanation plate) is fitted to the narrower end of a conically widening carrier sleeve 28. The connection between the contact element 24 and the carrier sleeve 28 may be permanent, for example by virtue of adhesion bonding, or it may be detachable, for instance by virtue of a screw coupling. The carrier sleeve 28 has at its wider sleeve end, in a manner not represented in any detail, suitable coupling structures for coupling to the focusing objective 18.

The laser source 12 and the scanner 16 are controlled by a control computer 30 which operates in accordance with a control program 34 stored in a memory 32. The control program 34 contains instructions (program code) that bring about, upon execution by the control computer 30, such a control of the location of the beam focus of the laser beam 14 that in the cornea of the eye 22 bearing against the contact element 24 an incision figure arises that permits the subsequent insertion of an intrastromal corneal ring implant.

For the purpose of elucidating various variants and particulars of this incision figure, reference will now be made to FIGS. 2 to 6. These illustrate the incision figure as it appears in the applaned (levelled) state of the cornea. After lifting of the contact between eye 22 and contact element 24 and return of the cornea to its originally curved shape, a change in the three-dimensional appearance of the incision figure generated may naturally arise.

For the purpose of better orientation, in all the Figures, including FIG. 1, a coordinate frame with the aforementioned x, y- and z-directions has been drawn in.

Figure 2:
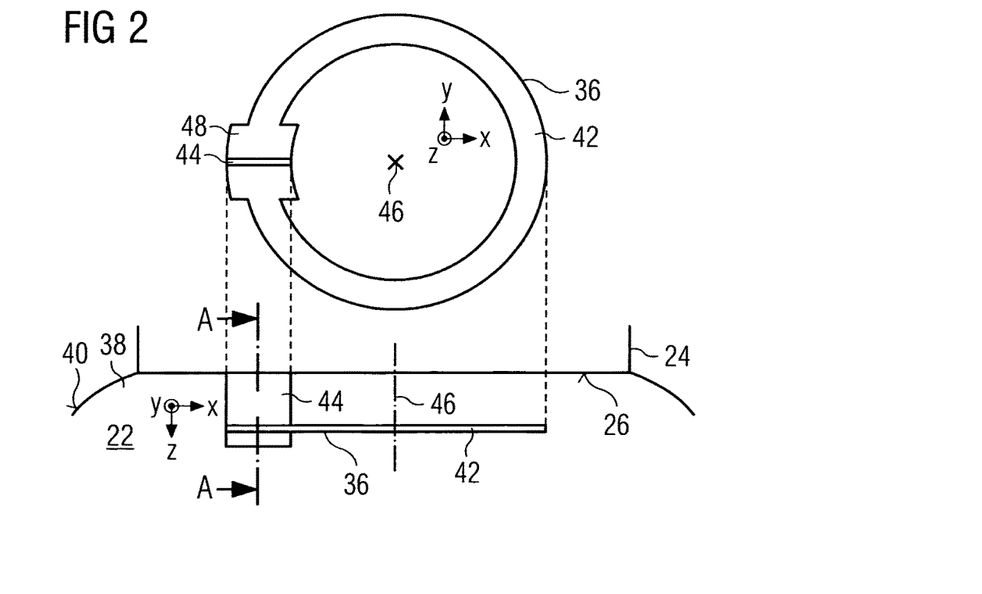
FIGS. 2 to 6: various variants of an incision figure that is capable of being generated in the cornea of an eye with the device shown in FIG. 1 and FIGS. 7 to 11: various exemplary cross-sectional geometries of an opening incision.

FIG. 2 shows, in its upper half, an exemplary embodiment of an intracorneal incision figure denoted generally by 36 in a view in a cross-section perpendicular to the z-direction; in its lower half, on the other hand, it shows a view of the same incision figure in a view perpendicular to the x-y transverse plane. In addition, in the lower half of FIG. 2 the contact element 24 with its abutment surface 26 facing towards the eye and also a cornea 38 of the eye 22 to be treated are indicated diagrammatically. The levelling of the cornea 38 as a consequence of the abutment of the eye 22 on the abutment surface 26 can be discerned; 40 denotes the anterior surface of the cornea, which is synonymous with the surface of the eye.

The incision FIG. 36 is composed of a ring incision 42 extending over a closed ring and situated totally deep within the cornea 38, and also of an opening incision 44 intersecting the ring incision 42 and extending from the corneal surface 40 to beyond the ring incision 42. In the exemplary case that is shown, the ring incision 42 is of annular design; its ring axis is indicated diagrammatically at 46 in the two halves of FIG. 2. The ring incision 42 is worked into the cornea 38 centrically relative to the pupillary axis or another central axis of the eye 22 (for instance, the optical axis); its inside diameter is sufficiently large in order that the ring incision 42 runs around the pupil, outside the latter. This avoids a direct visual impairment by the implant to be inserted. The radial width (radial relative to the ring axis 46) of the ring incision 42 is proportionate to the implant to be inserted and is in any case such that the implant, on the one hand, can be easily pushed into the tunnel formed by the ring incision 42 but, on the other hand, is held radially in this tunnel comparatively firmly and is only—if at all—slightly mobile.

The ring incision 42 has substantially constant radial width along its entire ring periphery, with the exception of a widening zone 48 designated in the following as a platform, where it is radially widened both radially inside and radially outside in comparison with the adjoining regions of the ring incision 42. The platform 48 is located where the opening incision 44 impinges on the ring incision 42. The peripheral extent of the platform 48 is small in comparison with the overall length of the ring incision 42 in the peripheral direction. The platform 48 preferentially extends over an angular length of no more than 40 degrees, better no more than 35 degrees and still better no more than 30 degrees.

The opening incision 44 is generated in the applaned state of the cornea 38 with a longitudinal extent perpendicular to the ring plane of the ring incision 42. 'Longitudinal extent' in this connection means the extent of the opening incision 44 from the corneal surface 40 as far as its end situated on the other side of the ring incision 42 deep within the cornea 38. In the exemplary case that is shown, said opening incision has substantially constant width over its entire longitudinal extent, this width being larger than the radial width of the ring incision 42 outside the platform 48. On the other hand, the platform 48 is so dimensioned in the radial direction that it has, at least in the region of overlap with the opening incision 44, a radial width that corresponds at least to the width of the opening incision 44. A radial protrusion of the opening incision 44 beyond the edges of the platform 48 is avoided in this way. In the exemplary case of FIG. 2 which is shown, the platform 48 has over its entire peripheral length a radial width that is substantially equal to the width of the opening incision 44. The transition of the platform 48 to the adjoining regions of the ring incision 42 occurs in FIG. 2 in step-like manner in a single step. The radial edges of the platform 48 run in this case in the form of circular arcs and are situated concentrically with the ring axis 46. Of course, a multiply-stepped transition is also possible.

In the exemplary case of FIG. 2 which is shown, the orientation of the opening incision 44 in the direction of its width is radial relative to the ring axis 46.

In the course of the generation of the incision FIG. 36, parts of the figure situated deeper within the cornea 38 are expediently generated before such figure parts that are situated less deeply within the cornea 38, in order to avoid shading effects and an impaired cutting action by virtue of figure parts situated higher up. For this reason, preferentially firstly that region of the opening incision 44 is prepared by which it protrudes axially beyond the ring incision 42 in the direction towards deeper-lying regions of the cornea 38. Then the ring incision 42, inclusive of its platform 48, is cut, whereby, for example, it is possible to proceed from radially inside to radially outside. This means that a start is made with the overhang of the platform 48 jutting out radially inside beyond the adjoining regions of the ring incision 42, and the cutting procedure terminates in the plane of the ring incision 42 with the radially outer overhang of the platform 48 beyond the adjoining regions of the ring incision 42. An advantageous aspect of such a way of proceeding is that gas bubbles arising in the course of the photodisruptions (occasionally designated in specialist circles as opaque bubble layer) are driven outwards, i.e. away from the pupil of the eye 22. But it is of course also conceivable to proceed in the direction from radially outside to radially inside and firstly to cut the radially outer overhang of the platform 48 before the main part of the ring incision 42 and, finally, the radially inner overhang of the platform 48 are cut.

After the ring incision 42 has been cut, the part of the opening incision 44 running above said ring incision is cut, to be specific expediently starting from the ring incision 42 and at increasingly smaller distance from the anterior surface 40 of the cornea.

In the elucidation of the variants shown in FIGS. 3 to 6 the same reference symbols as previously have been drawn upon, but supplemented by a lower-case letter. To the extent that nothing else arises in the following, reference is made to the above remarks for the purpose of elucidating the elements denoted by the same reference symbols.

Figure 3:
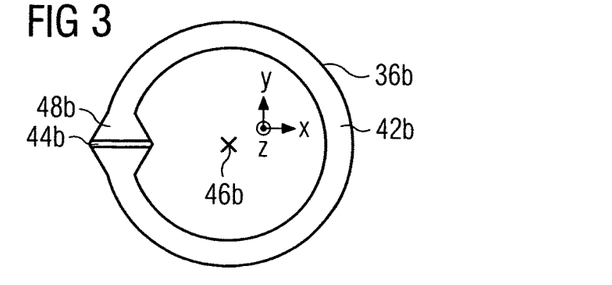

In the variant shown in FIG. 3 the ring incision 42b is realised, just as previously, as a full-ring incision, whereby, however, its platform 48b is configured both radially inside and radially outside in triangular or sawtooth form and accordingly becomes continuously radially narrower from a central region of greatest radial width and finally merges with the adjoining regions of constant radial width of the ring incision 42b. The opening incision 44b runs with radial orientation with respect to the ring axis 46b and extends in the region of overlap with the ring incision 42b from the radially inner vertex of the triangle to the radially outer vertex of the triangle of the platform 48b.

Figure 4:
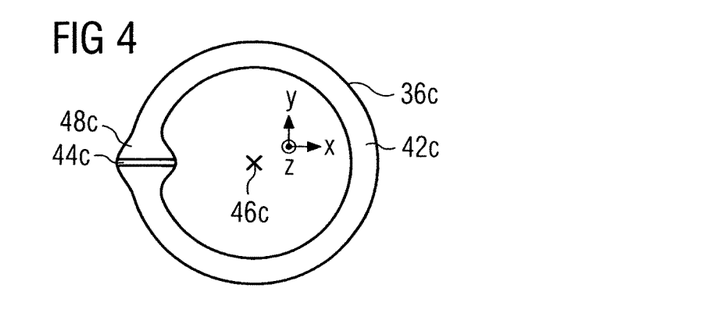

The variant shown in FIG. 4 is similar to that shown in FIG. 3 but differs from the latter by virtue of a bulbous/spheroidal configuration of the platform 48c both radially inside and radially outside. Furthermore, the opening incision 44c impinges on the ring incision 42c in the region of maximal radial width of the platform 48c.

It will be understood that arbitrary different platform geometries are possible.

Figure 5:
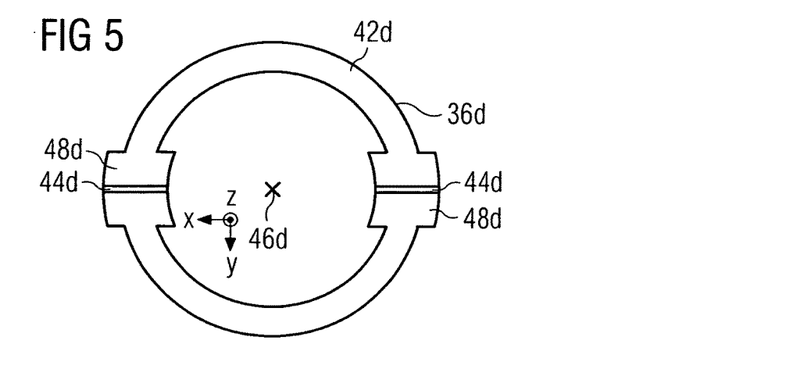

FIG. 5 shows a variant in which the incision FIG. 36d exhibits a total of two opening incisions 44d which in two diametrically opposed regions of the ring incision 42d, which once again is realised as a full-ring incision, impinge on said ring incision. Assigned to each of the opening incisions 44d, the ring incision 42d exhibits a platform 48d which in the exemplary case shown in FIG. 5 is configured in the manner of the platform 48 shown in FIG. 2. Of course, use may alternatively be made here of the platform configurations shown in FIGS. 3 and 4 or optionally other platform configurations not represented in any detail.

It should be pointed out that platforms may, in principle, be provided in arbitrary number and at arbitrary positions.

Figure 6:
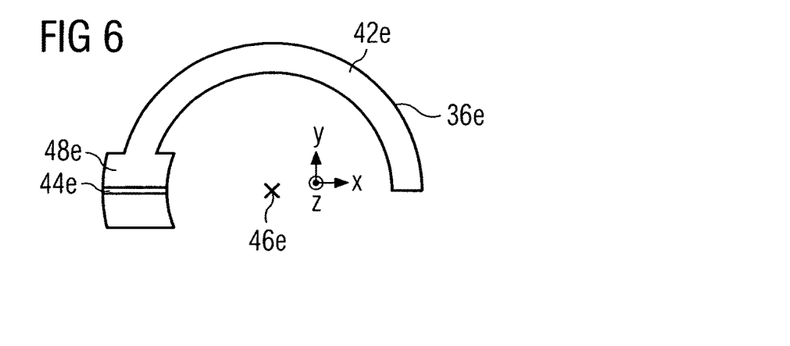

The variant shown in FIG. 6 differs from the previous variants in that the ring incision 42e extends only over a part of a full ring periphery and in the concrete exemplary case is realised as a semi-ring incision—that is to say, as an incision that extends approximately over half a ring periphery. The platform 48e is formed at one of the peripheral ends of the ring incision 42e. This variant is suitable for such indications that require the implantation merely of a semi-ring implant. It will be understood that the semi-ring incision 42e can be generated in various angular positions around the pupillary axis, depending on where the implant in question is to be placed.

Overall, ring incisions can be generated in the cornea by laser technology in arbitrary number, angular length and angular position. Each of these ring incisions can be combined with one or more platforms.

Reference will now be made to FIGS. 7 to 11, in which various exemplary variants of an opening incision are shown such as may be provided in the incision figures shown in FIGS. 2 to 6. Shown in each instance in FIGS. 7 to 11 is an incision through the cornea 38*f* . . . 38*k* of the eye to be treated, the anterior surface of the cornea being denoted by 40*f* . . . 40*k*, the posterior surface of the cornea being denoted by 50*f* . . . 50*k*, and the region of the anterior chamber of the eye being denoted by 52*f* . . . 52*k*. The representations shown in FIGS. 7 to 11 correspond to an incision along the line A-A in FIG. 2.

Figure 7:
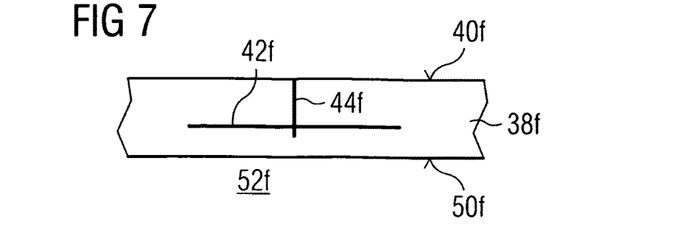

FIG. 7 shows a variant with an opening incision 44*f* which extends as far as the anterior surface 40*f* of the cornea, so that the implant can be inserted into the ring incision 42*f* directly from outside through the opening incision 44*f*. The opening incision 44*f* according to FIG. 7 has a straight progression, running substantially perpendicular to the ring plane of the ring incision 42.

Figure 8:
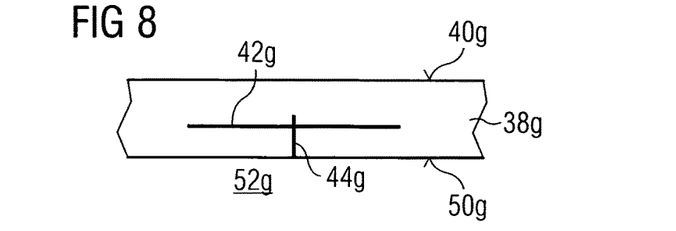

In contrast. FIG. 8 shows a variant with an opening incision 44*g* which extends from the posterior surface 50*g* of the cornea in the direction towards the ring incision 42*g* and in this way creates an opening towards the anterior chamber 52*g* of the eye, through which an implant can be introduced into the ring incision 42*g*. Similarly as in the case of FIG. 7, the opening incision 44*g* according to FIG. 8 is of rectilinear design, running substantially perpendicular to the ring plane of the ring incision 42*g*.

Figure 9:
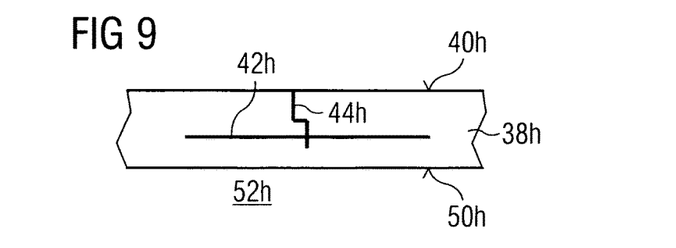
Figure 10:
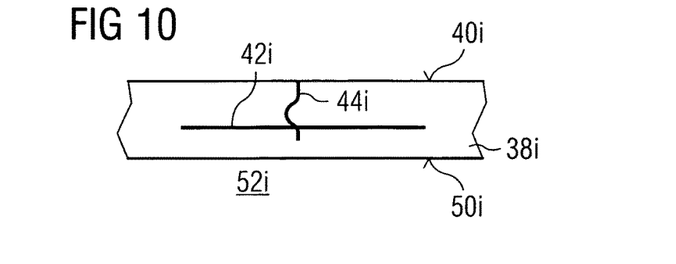
Figure 11:
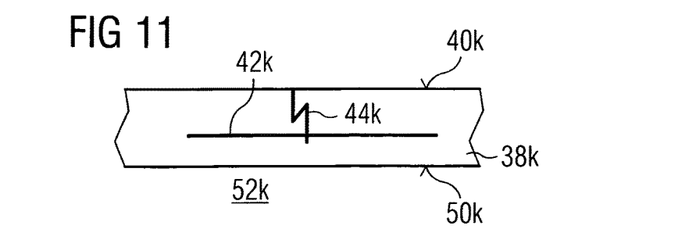

FIGS. 9 to 11 show variants with an opening incision that has a non-rectilinear progression. It will be understood that in this respect numerous different cross-sectional geometries of the opening incision are conceivable. In exemplary manner in FIG. 9 a variant with an opening incision 44*h* bending twice sharply is shown which has two sharp bends bending in opposite directions, so that upstream and downstream of the two sharp bends the opening incision 44*h* has the same direction of progression. In the exemplary case shown in FIG. 9 the sharp bends are 90° sharp bends.

FIG. 10 shows a variant with a singly undulating opening incision 44*i*, in which connection it will be understood that the opening incision may, if desired, may be multiply-undulating.

FIG. 11 shows, on the other hand, a variant of an opening incision 44*k* likewise bending twice sharply, whereby, however, both sharp-bend angles are acute, so that the opening incision 44*k* has a progression in the manner of an undercut.

It will be understood that the incision geometries of FIGS. 9 to 11 may, if desired, also be used for an opening incision that starts from the posterior surface of the cornea.

The invention claimed is:

1. Device for machining a cornea of a human eye with focused pulsed laser radiation, the device comprising:
   a plurality of controllable components configured to set a location of the radiation focus; and
   a control computer configured to control the components according to a control program to create an incision figure in the cornea that permits insertion of an intrastromal corneal ring implant, the incision figure comprising:
      at least one ring incision of annular design situated within the cornea, the ring incision lying parallel to a ring plane perpendicular to a ring axis of the ring incision, the ring incision having a radial width radial relative to the ring axis and having a peripheral length measured in a peripheral direction of the ring incision; and
      at least one opening incision extending at right angles to the ring plane from an anterior surface of the cornea or from a posterior surface of the cornea to at least the ring incision, the opening incision oriented substantially radially relative to the ring axis when viewed in a cross-section perpendicular to the ring axis,
      the ring incision comprising a widening zone and a remaining portion that comprises the rest of the ring incision excluding the widening zone, the opening incision impinging on the ring incision at the widening zone;
      the widening zone:
         comprising a plurality of transitions and a plurality of radial edges, a radial edge comprising a circular arc concentric with the ring axis, a transition connecting a radial edge to the remaining portion and parallel to the opening incision;
         having a larger radial width than that of the remaining portion, the remaining portion having a continuous radial width; and
         having a peripheral length that is at most twenty percent of the peripheral length of the ring incision.

2. Device according to claim 1, wherein the widening zone has a radial widening inside and outside of the ring incision compared to the rest of the ring incision.

3. Device according to claim 1, wherein the opening incision, when viewed in a cross-section perpendicular to the ring plane and through the ring axis, runs substantially rectilinearly.

4. Device according to claim 1, wherein the opening incision, when viewed in a cross-section perpendicular to the ring plane and through the ring axis, runs at least along a portion in curved or bent manner.

5. Device according to claim 1, wherein the opening incision crosses the ring incision in the direction from the anterior surface or posterior surface of the cornea and extends beyond said ring incision.

6. Device according to claim 1, wherein the opening incision impinges on the ring incision in a region of greatest radial width of the widening zone and extends there substantially over the entire radial width of the widening zone.

7. Device according to claim 1, wherein the ring incision forms a ring that is closed in the peripheral direction.

8. Device according to claim 1, wherein the ring incision forms a partial ring in the peripheral direction.

9. Device according to claim 1, wherein the incision figure includes two or more partial ring incisions that form a circular pattern, each partial ring incision having at least one opening incision.

10. Device according to claim 1, wherein the incision figure includes at least one ring incision with a single opening incision.

11. Device according to claim 1, wherein the incision figure includes at least one ring incision with two or more opening incisions.

12. Device according to claim 1, wherein the laser radiation has pulse durations within the range of less than 1 picosecond.

13. Process for treating a human eye, comprising:
   making pulsed laser radiation available, the laser radiation having a radiation focus,
   directing the laser radiation onto a human cornea,
   controlling the radiation focus of the laser radiation to create an incision figure in the cornea permitting insertion of at least one intrastromal corneal ring implant, the incision figure comprising at least one ring incision and at least one opening incision;
   the at least one ring incision having an annular design and situated within the cornea, the ring incision lying parallel to a ring plane perpendicular to a ring axis of the ring incision, the ring incision having a radial width radial relative to the ring axis and having a peripheral length measured in a peripheral direction of the ring incision; and the at least one opening incision extending at right angles to the ring plane from an anterior surface of the cornea or from a posterior surface of the cornea to at least the ring incision, the opening incision oriented substantially radially relative to the ring axis when viewed in a cross-section perpendicular to the ring axis, the ring incision comprising a widening zone and a remaining portion that comprises the rest of the ring incision excluding the widening zone, the opening incision impinging on the ring incision at the widening zone;

the widening zone:

comprising a plurality of transitions and a plurality of radial edges, a radial edge comprising a circular arc concentric with the ring axis, a transition connecting a radial edge to the remaining portion and parallel to the opening incision;

having a larger radial width than that of the remaining portion, the remaining portion having a continuous radial width; and having a peripheral length that is at most twenty percent of the peripheral length of the ring incision.

14. Process according to claim 13, wherein the widening zone has a radial widening inside and outside of the ring incision compared to the rest of the ring incision.

15. Process according to claim 13, wherein the opening incision, when viewed in a cross-section perpendicular to the ring plane and through the ring axis, runs substantially rectilinearly.

16. Process according to claim 13, wherein the opening incision, when viewed in a cross-section perpendicular to the ring plane and through the ring axis, runs at least along a portion in curved or bent manner.

17. Process according to claim 13, wherein the opening incision crosses the ring incision in the direction from the anterior surface or posterior surface of the cornea and extends beyond said ring incision.

18. Process according to claim 13, wherein the opening incision impinges on the ring incision in a region of greatest radial width of the widening zone and extends there substantially over the entire radial width of the widening zone.

19. Process according to claim 13, wherein the ring incision forms a ring that is closed in the peripheral direction.

20. Process according to claim 13, wherein the ring incision forms a partial ring in the peripheral direction.

21. Process according to claim 13, wherein the incision figure includes two or more partial ring incisions that form a circular pattern, each partial ring incision having at least one opening incision.

22. Process according to claim 13, wherein the incision figure includes at least one ring incision with a single opening incision.

23. Process according to claim 13, wherein the incision figure includes at least one ring incision with two or more opening incisions.

24. Process according to claim 13, wherein the laser radiation has pulse durations within the range of less than 1 picosecond.

* * * * *